United States Patent
Thiel et al.

(10) Patent No.: US 6,939,991 B2
(45) Date of Patent: Sep. 6, 2005

(54) PREPARATION OF ACRYLIC ACID

(75) Inventors: Joachim Thiel, Neustadt (DE); Ulrich Hammon, Mannheim (DE); Dieter Baumann, Frankenthal (DE); Jörg Heilek, Bammental (DE); Jürgen Schröder, Ludwigshafen (DE); Klaus Joachim Müller-Engel, Stutensee (DE)

(73) Assignee: BASF Aktiengesellschaft, Ludwigshafen (DE)

(*) Notice: Subject to any disclaimer, the term of this patent is extended or adjusted under 35 U.S.C. 154(b) by 41 days.

(21) Appl. No.: 10/465,613

(22) Filed: Jun. 20, 2003

(65) Prior Publication Data

US 2004/0073063 A1 Apr. 15, 2004

(30) Foreign Application Priority Data

Oct. 10, 2002 (DE) .......................................... 102 47 240

(51) Int. Cl.⁷ ............................................. C07C 51/16
(52) U.S. Cl. ........................ 562/545; 562/523; 562/524; 562/527; 562/530; 562/531; 562/532; 562/537; 562/538; 562/542; 562/544
(58) Field of Search ................................ 526/523, 524, 526/527, 531, 532, 545, 544, 542

(56) References Cited

U.S. PATENT DOCUMENTS 6,498,272 B1 * 12/2002 Schroder et al. ............ 562/600

FOREIGN PATENT DOCUMENTS

| DE | 199 24 532 | 11/2000 |
| DE | 199 24 533 | 11/2000 |
| DE | 101 56 016 | 6/2003 |
| DE | 102 35 847 | 8/2003 |
| DE | 102 23 058 | 12/2003 |
| DE | 102 43 625 | 4/2004 |
| WO | WO 01/77056 | 10/2001 |

* cited by examiner

Primary Examiner—Johann Richter
Assistant Examiner—Karl Puttlitz
(74) Attorney, Agent, or Firm—Oblon, Spivak, McClelland, Maier & Neustadt, P.C.

(57) ABSTRACT

In a process for preparing acrylic acid, an acrylic acid-containing product gas mixture obtained by catalytic gas phase partial oxidation of a $C_3$ precursor of acrylic acid, after direct cooling with a quench liquid, is fractionally condensed in a separating column provided with internals, rising into itself with sidestream takeoff of crude acrylic acid, and the acrylic acid oligomers which form are dissociated and the resulting dissociation gas is subjected to a countercurrent rectification before it is recycled.

20 Claims, No Drawings

PREPARATION OF ACRYLIC ACID

The present invention relates to a process for preparing acrylic acid by generating an acrylic acid-containing product gas mixture by heterogeneously catalyzed gas phase partial oxidation of at least one $C_3$ precursor of acrylic acid with molecular oxygen over catalysts in the solid state at elevated temperature, initially reducing the temperature of the hot acrylic acid-containing product gas mixture by direct cooling with a quench liquid 1 and subsequently passing the cooled product gas mixture which may possibly contain portions of evaporated quench liquid 1 into a condensation column equipped with separating internals, allowing it to rise into itself within the condensation column, thus fractionally condensing it, and withdrawing crude acrylic acid as the target product from the condensation column in a sidestream and withdrawing bottom liquid comprising acrylic acid oligomers from the bottom of the condensation column or removing high boiler fraction comprising acrylic acid oligomers or a mixture of such bottom liquid comprising acrylic acid oligomers and high boiler fraction from the condensation column via a sidestream takeoff disposed below the sidestream takeoff for the crude acrylic acid and using it as a quench liquid 1, recirculating the portion of the quench liquid 1 which is not evaporated on cooling the product gas mixture, optionally via the bottom or via the high boiler takeoff of the condensation column or via both and also optionally via a heat exchanger, discharging a portion of the quench liquid 1 from this circuit as a bleed stream and feeding it to a dissociation vessel and dissociating therein the acrylic acid oligomers contained in the bleed stream of the quench liquid 1 at elevated temperature to acrylic acid, and recycling the dissociation gases comprising acrylic acid and escaping from the liquid phase in gaseous form into the circuit of the quench liquid 1 or into the condensation column or into the circuit of the quench liquid 1 and into the condensation column, either in gaseous, condensed or partially condensed form.

The term acrylic acid or crude acrylic acid expresses that the acrylic acid withdrawn via the sidestream takeoff is not a pure product, but rather a mixture which, in addition to acrylic acid (generally $\geq 90\%$, or $\geq 95\%$ of the total weight) also comprises typical by-products of the gas phase oxidation, for example water, lower aldehydes (e.g. furfurals, acrolein, benzaldehyde), lower carboxylic acids (e.g. acetic acid, propionic acid), etc. One way of obtaining acrylic acid is by heterogeneously catalyzed gas phase partial oxidation of $C_3$ precursors of acrylic acid (this term encompasses those chemical compounds which are obtainable formally by reduction of acrylic acid; examples of well-known $C_3$ precursors of acrylic acid include propane, propene, acrolein, propionaldehyde and propionic acid) using molecular oxygen over catalysts in the solid state at elevated temperature. The starting gases specified, generally diluted with inert gases, e.g. nitrogen, $CO_2$, saturated hydrocarbons and/or steam, are passed over transition metal mixed oxide catalysts in a mixture with molecular oxygen at elevated temperatures and also optionally elevated pressure and converted oxidatively to the product gas mixture comprising acrylic acid and secondary components, for example furfurals, benzaldehyde and maleic anhydride, from which the acrylic acid has to be removed.

Starting from propionaldehyde and/or propionic acid, the heterogeneously catalyzed gas phase partial oxidation with molecular oxygen is at least partially an oxidative dehydrogenation.

DE-A 199 24 533 discloses a process, as described at the outset, for preparing acrylic acid by carrying out a basic separation of crude acrylic acid by fractional condensation of the product gas mixture of the heterogeneously catalyzed gas phase partial oxidation. Similar processes of basic separation of crude acrylic acid are disclosed by DE-A 199 24 532, WO 01/77056, DE-A 10156016, DE-A 10243625, DE-A 10223058 and DE-A 10235847.

The dissociation of the acrylic acid oligomers has the aim of increasing the yield of product of value.

The cause of the formation of acrylic acid oligomers is that acrylic acid present in the condensed phase forms acrylic acid oligomers (Michael adducts) by reversible Michael addition to itself and also to acrylic acid dimers being formed (the term acrylic acid oligomers in this document always refers to the corresponding Michael adducts and not to acrylic acid oligomers formed by free radical polymerization).

The presence of water, the unavoidable by-product of a gas phase catalytic oxidative preparation of acrylic acid, and also elevated temperatures support the formation of acrylic acid oligomers.

Since acrylic acid oligomers have a higher boiling temperature than acrylic acid, they accumulate in the high boiler region (e.g. in the bottom liquid) in both a distillative removal of acrylic acid and in a fractional condensation of the product gas mixture of a gas phase catalytic oxidative acrylic acid generation.

The action of elevated temperature with simultaneous removal of the acrylic acid formed enables the Michael addition to be reversed.

In the examples of DE-A 199 24 533, the dissociation vessel (reactor) is always attached to a guard column (e.g. a short column filled with Raschig rings), through which the acrylic acid-containing dissociation gases are removed gaseously and without reflux and recycled after subsequent condensation.

A disadvantage of such a procedure is that the purity of the crude acrylic acid withdrawn from the condensation column is not completely satisfactory. This is true especially when the crude acrylic acid is further purified crystallizatively, extractively and/or rectificatively, and resulting mother liquor, bottom liquid, raffinate and/or condensate are recycled into the condensation column for the fractional condensation of the product gas mixture of the gas phase partial oxidation.

It is an object of the present invention to provide an improved process for basic separation of acrylic acid from the product gas mixture of the heterogeneously catalyzed gas phase partial oxidation.

We have found that this object is achieved by a process for preparing acrylic acid by generating an acrylic acid-containing product gas mixture by heterogeneously catalyzed gas phase partial oxidation of at least one $C_3$ precursor of acrylic acid with molecular oxygen over catalysts in the solid state at elevated temperature, initially reducing the temperature of the hot acrylic acid-containing product gas mixture by direct cooling with a quench liquid 1 and subsequently passing the cooled product gas mixture which may possibly contain portions of evaporated quench liquid 1 into a condensation column equipped with separating internals, allowing it to rise into itself within the condensation column, thus fractionally condensing it, and withdrawing crude acrylic acid as the target product from the condensation column in a sidestream and withdrawing bottom liquid comprising acrylic acid oligomers from the bottom of the condensation column or removing high boiler fraction comprising acrylic acid oligomers or a mixture of such bottom liquid comprising acrylic acid oligomers and high boiler fraction from the condensation column via a sidestream takeoff disposed below the sidestream takeoff for the crude acrylic acid and using it as a quench liquid 1, recirculating the portion of the quench liquid 1 which is not evaporated on cooling the product gas mixture, optionally via the bottom or via the high boiler takeoff of the condensation column or via both and also optionally via a heat exchanger, discharging a portion of the quench liquid 1 from this circuit as a bleed stream and feeding it to a dissociation vessel and dissociating therein the acrylic acid oligomers contained in the bleed stream of the quench liquid 1 at elevated temperature to acrylic acid, and recycling the dissociation gases comprising acrylic acid and escaping from the liquid phase in gaseous form into the circuit of the quench liquid 1 or into the condensation column or into the circuit of the quench liquid 1 and into the condensation column, either in gaseous, condensed or partially condensed form, which comprises subjecting the dissociation gases to a countercurrent rectification before they are recycled.

The advantage of the process according to the invention is in particular that when the yield of crude acrylic acid is the same, the content of by-products which boil slightly higher than acrylic acid at atmospheric pressure (1 bar) (e.g. benzaldehyde, furfurals and maleic anhydride) in the crude acrylic acid withdrawn from the condensation column via the sidestream takeoff is reduced. At the same secondary component content, this corresponds conversely to an increased yield of crude acrylic acid. This is significant in particular when the crude acrylic acid is further purified crystallizatively, extractively and/or rectificatively and resulting mother liquor, bottom liquid, raffinate and/or condensate are recycled into the condensation column for the fractional condensation of the product gas mixture of the gas phase partial oxidation.

This is the case especially when the $P_F:R_F$ ratio of the content $P_F$ of furfurals in the crude acrylic acid withdrawn, expressed as a % by weight of the acrylic acid contained in the crude acrylic acid, to the content $R_F$ of furfurals in the pure product obtained by this, for example, crystallizative, further purification, likewise expressed as a % by weight of the acrylic acid contained in the pure product, is $\geq 300$, preferably $\geq 1000$, more preferably $\geq 2000$, but generally $\leq 50\ 000$.

In the countercurrent rectification to be used according to the invention on the dissociation gases, the dissociation gases and reflux liquid are conducted in countercurrent to each other through a rectification column.

The rectification column used for this purpose may be any type of rectification column known per se. These are all columns comprising separating internals, and examples of useful internals include structured packings, random packings and/or trays. In principle, it is also possible to use columns having rotating internals, known as rotation columns, which atomize the reflux liquid into droplets.

According to the invention, preference is given to using a rectification column for the dissociation gases which comprises only trays and/or structured packings. Advantageous trays are dual-flow trays and, particularly advantageously, the rectification column comprises exclusively dual-flow trays as separating internals.

In this document, dual-flow trays refer to plates having simple passages (holes, slots, etc.). The gas rising in the rectification colum and the reflux liquid falling in the rectification column flow in opposite directions through the same passages. The cross section of the passages is adapted in a manner known per se to the loading of the rectification column. When it is too small, the rising dissociation gas flows at such a high rate through the passages that the reflux liquid falling in the rectification column is substantially entrained without separation. When the cross section of the passages is too large, rising dissociation gas and falling reflux substantially flow past each other without exchange and the tray is at risk of running dry. Customarily, dual-flow trays have no downcomer which connects them to the next tray. It will be appreciated that each dual-flow tray may be joined flush to the walls of the rectification column. However, they may also be connected to it via separators. In contrast to hydraulically sealed crossflow trays, dual-flow trays run dry with decreasing loading of the rectification column.

According to the invention, the dual-flow tray rectification column which can be used according to the invention for the dissociation gases may advantageously contain up to 60 dual-flow trays. In general, it will contain from 30 to 50 dual-flow trays. Advantageously, these have an orifice ratio (the D:U ratio formed from the proportion of the surface area of the tray which is permeable to the dissociation gas (D) and the total surface area of the tray (U)) of from 10 to 20%, preferably from 10 to 15%.

The passages of the dual-flow trays are preferably circular holes having a uniform circle diameter within the tray. This diameter is advantageously from 10 to 30 mm. In the upper section of the column, it is advantageously from 10 to 20 mm, or from 10 to 15 mm, and in the lower section of the column, it is advantageously from 20 to 30 mm. The circular holes are also preferably arranged uniformly over the individual dual-flow trays in strict triangular pitch (cf. DE-A 10230219). Also, the punched burr of the passages punched out in the dual-flow trays to be used according to the invention in the rectification column to be used according to the invention preferably points downward. Customarily, the dual-flow trays are arranged equidistantly in the rectification column. Typically, the tray separation is from 300 to 500 mm. According to the invention, a tray separation of 400 mm is also advantageous. The thermal dissociation to be integrated according to the invention can be carried out in a simple manner in a forced circulation-decompression evaporator. However, instead of a forced circulation-decompression evaporator, it is also possible to use, for example, a Robert evaporator or a natural circulation evaporator. Dissociation vessel (reactor) and rectification column may either be spatially separated or else be seamlessly joined together. In both cases, the portion of the quench liquid 1 discharged from the circuit in the process according to the invention is advantageously conducted not directly into the dissociation vessel, but rather via the rectification column attached thereto, preferably via its lower section (e.g. lower third). Advantageously, the feed is effected to the fourth to tenth dual-flow tray of the rectification column (counted from below). The dissociation temperature in the process according to the invention is advantageously from 160 to 190° C., preferably from 165 to 175° C. The working pressure selected for the dissociation will advantageously be slightly above (e.g. 100 mbar above) the pressure in the quench circuit 1. A typical range for working pressures suitable for the dissociation is from 1 to 2 bar.

It may otherwise be advantageous according to the invention to carry out the dissociation with the addition of an inorganic salt whose addition to an aqueous solution of a strong Brönsted acid shifts the pH of the aqueous solution into the alkaline region as a catalyst, as recommended, for example, by DE-C 2 407 236. Based on the amount of discharged quench liquid 1 to be subjected to dissociation, the amount of basic dissociation catalyst to be added will generally be from 0.1 to 5% by weight. Examples of dissociation catalysts suitable according to the invention include KOH, $K_2CO_3$, $KHCO_3$, NaOH, $Na_2CO_3$, $NaHCO_3$, LiOH, $Li_2CO_3$ and $CaCO_3$. In other words, suitable dissociation catalysts are in particular the alkali metal and/or alkaline earth metal salts of weakly organic or inorganic Brönsted acids for example phosphoric acid, boric acid, carbonic acid, formic acid or acetic acid. In other words, useful dissociation catalysts are in particular alkali metal and/or alkaline earth metal phosphates, borates, carbonates, hydrogencarbonates, formates and acetates.

The dissociation catalysts will preferably be selected in such a way that they are soluble in the discharged quench liquid 1 under the dissociation conditions. According to U.S. Pat. No. 4,293,347, the presence of dialkyl phthalates also has an advantageous effect on the relevant dissociation.

When the dissociation is carried out continuously (preference is given to carrying out the process according to the invention continuously), the residence time in the dissociation reactor should be from 0.5 to 4 h. As described in U.S. Pat. No. 5,733,075 and also in DE-A 4101879, the dissociation of acrylic acid oligomers can in principle also be carried out without the addition of dissociation catalysts. Preference is given to this procedure according to the invention. However, it is also possible to use acidic dissociation catalysts. Useful catalysts include dodecylbenzenesulfonic acid, p-toluenesulfonic acid, sulfuric acid or the solid acid catalysts of JP-A 178949.

It is advantageous according to the invention when the dissociation reactor (the dissociation vessel) and the rectification column (it is also advantageous when there is only flow through the rectification column) for the dissociation gas is flowed through by an oxygen-containing gas. Examples of useful gases include air, oxygen-depleted air and/or cycle gas. Cycle gas refers to the gas which remains when the constituents which can be easily condensed (primarily water and less volatile constituents) are substantially condensed out of the product gas mixture of the heterogeneously catalyzed gas phase partial oxidation in the condensation column. It generally leaves the condensation column at its top and may, for example, have the following composition typical for the process according to the invention in the case of a two-stage gas phase partial oxidation starting from propylene:

0.2651% by weight of acrylic acid,
0.0989% by weight of acetic acid,
2.9333% by weight of water,
0.0059% by weight of formic acid,
0.1720% by weight of acrolein,
0.0002% by weight of propionic acid,
0.0002% by weight of furfurals,
0.0013% by weight of allyl formate,
4.7235% by weight of oxygen,
2.1171% by weight of $CO_2$,
0.6921% by weight of CO,
0.6466% by weight of propane,
0.3161% by weight of propylene and
88.0277% by weight of nitrogen.

From an application point of view, it is advantageous to conduct the oxygen-containing gas (referred to hereinbelow as "support gas") directly into the dissociation reactor, whence it is fed automatically to the rectification column together with the dissociation gases. However, it could also be introduced directly into the rectification column (advantageously below the first tray (from below)). The use of the oxygen-containing gas on the one hand has a polymerization-inhibiting effect and, on the other hand, supports the conveyance of the dissociation gases into the rectification column. In addition, it reduces the partial dissociation gas pressure. Instead of an oxygen-containing gas, an NO-containing gas can also be used. Both in the case of oxygen and in the case of NO, the remaining gas constituents are inert gas.

Advantageously, the rectification column (like the condensation column) is insulated from the environment. The reflux liquid may be generated by direct and/or indirect cooling. According to the invention, the method of direct cooling is advantageously applied. To this end, the simplest way is to feed the dissociation gases (or their mixture with support gas) which leave the rectification column at its top to a quench apparatus 2. Useful quench apparatus 2 includes all apparatus known for this purpose from the prior art (e.g. spray scrubbers, Venturi scrubbers, bubble columns or other apparatus having sprayed surfaces), although preference is given to using Venturi scrubbers or spray coolers. Preference is given to a cocurrent apparatus (e.g. one having an impingement plate nozzle). For indirect cooling of the quench liquid 2, this is customarily conducted through a heat transferor or heat exchanger. In this regard, all common heat transferors or heat exchangers are suitable. Preference is given to tube bundle heat exchangers, plate heat exchangers and air coolers. Suitable cooling media are air in the case of corresponding air coolers and cooling liquids, especially water, in the case of the other cooling apparatus.

From an application point of view, the quench liquid 2 used is advantageously a portion of the condensate formed on quenching 2. The other portion of the condensate formed on quenching 2 is recycled as reflux liquid into the top of the rectification column. Typically, the temperature of the quench liquid 2 immediately before its use for quenching 2 is about 30° C., whereas the reflux liquid is typically recycled into the rectification column at about 60° C. The dissociation gases themselves or their mixture with support gas leave the rectification column at its top generally at a temperature of from 90 to 100° C. It will be appreciated that the dissociation gas quench (the quench circuit 2) may also be integrated into the rectification column.

The mass ratio of the reflux liquid recycled into the rectification column to the discharged quench liquid 1 fed to the dissociation apparatus is typically $\geq 2$. It is frequently from 2 to 10 and preferably from 4 to 8.

It will be appreciated that the dissociation gas rectification column has to be operated with polymerization inhibition. Useful polymerization inhibitors for this purpose are in principle all polymerization inhibitors known from the prior art. Examples thereof include phenothiazine (PTZ) and p-methoxyphenol (MEHQ). Frequently, the latter two are used in combination. To this end, they are advantageously added dissolved in pure acrylic acid.

However, the polymerization inhibition of the quench circuit 2 and of the rectification column for the dissociation gases can also be achieved in a particularly elegant manner by adding a portion of the discharged, polymerization-inhibited, i.e. polymerization inhibitor-containing, quench liquid 1 to the quench circuit 2. The quench liquid 2 then typically contains, for example, from 0.01 to 0.02% by weight of MEHQ and from 0.01 to 0.02% by weight of PTZ.

According to the invention, the dissociation gas or mixture of dissociation gas and support gas leaving the quench circuit 2 in a cooled state may be recycled either into the quench circuit 1 and/or into the condensation column. This may be effected either in liquid or else in gaseous form.

According to the invention, preference is given to effecting this recycling in gaseous form. Advantageously, recycling is effected into the bottom space of the condensation column. This recycling may either be effected immersed into the bottom liquid or else above the liquid level of the bottom liquid and below the first tray of the condensation column. From an application point of view, the bottom space of the condensation column advantageously contains a drop separator (e.g. a centrifugal drop separator), in order to suppress entrainment of bottom liquid droplets by rising gas.

In the process according to the invention, the involatile residue remaining in the dissociation reactor is generally disposd of, for example incinerated. The addition of an organic solvent, e.g. methanol, maintains the involatile dissociation residue in the fluid state if required. Instead of methanol, it is also possible to use other hydrophilic organic solvents, e.g. ethanol or organic acids (e.g. ethylhexanoic acid, propionic acid) or residues from the preparation of these acids. It is also emphasized at this point that an inert organic liquid which has a higher boiling point than acrylic acid and maintains the quench liquid 1 in a fluid state may, if required, be added to the quench liquid 1 to be used in the process according to the invention. Useful high-boiling inert organic liquids are in particular all of those which are recommended in DE-A 2136396 and in DE-A 4308087.

These are substantially liquids whose boiling point at atmospheric pressure is above 160° C. Examples include ethylhexanoic acid, N-methylpyrrolidone, middle oil fractions from paraffin distillation, diphenyl ether, diphenyl or mixtures of the abovementioned liquids, for example a mixture of from 70 to 75% by weight of diphenyl ether and from 25 to 30% by weight of diphenyl. It is advantageous to use a mixture consisting of a mixture of from 70 to 75% by weight of diphenyl ether and from 25 to 30% by weight of diphenyl, and also, based on this mixture, from 0.1 to 25% by weight of o-dimethyl phthalate. In the abovementioned case, at least a portion of the inert organic liquid used will evaporate in the dissociation. When a portion of the organic liquid remains in the dissociation residue, it may be fed to a workup in which the solvent used is removed, for example distillatively, and recycled into the quench circuit 1. The remaining high boilers are disposed of.

Typically, the acrylic acid-containing product gas mixture of a heterogeneously catalyzed gas phase partial oxidation of $C_3$ precursors of acrylic acid using molecular oxygen over catalysts in the solid state has the following composition (especially when the $C_3$ precursor used is propylene):

from 1 to 30% by weight of acrylic acid,
from 0.05 to 10% by weight of molecular oxygen,
from 1 to 30% by weight of water,
from >0 to 5% by weight of acetic acid,
from >0 to 3% by weight of propionic acid,
from >0 to 1% by weight of maleic acid and/or maleic anhydride,
from 0 to 2% by weight of acrolein,
from 0 to 1% by weight of formaldehyde,
from >0 to 1% by weight of furfurals,
from >0 to 0.5% by weight of benzaldehyde,
from 0 to 1% by weight of propylene, and the remainder of inert gases, e.g. nitrogen, carbon monoxide, carbon dioxide, methane and/or propane.

Typically, the product gas mixture, based on acrylic acid present, comprises $\geq 0.005$ mol %, frequently $\geq 0.03$ mol %, of furfurals. However, the furfural content on this basis is generally $\leq 3$ mol %.

The gas phase partial oxidation itself may be carried out as described in the prior art. Starting from propylene, the gas phase partial oxidation may be carried out, for example, in two successive oxidation stages, as described in EP-A 700714 and EP-A 700893. However, it will be appreciated that the gas phase partial oxidations cited in DE-A 19740253 and also in DE-A 19740252 may also be used.

For the purposes of forming a small amount of secondary components, preference is given to carrying out the propylene gas phase partial oxidation as described in DE-A 10148566. The propylene source used for this purpose may be polymer grade propylene or chemical grade propylene according to DE-A 10232748. When the $C_3$ precursor used is propane, the partial oxidation may be carried out as described in DE-A 10245585.

Frequently, the temperature of the product gas mixture leaving the gas phase partial oxidation is from 150 to 350° C., in many cases from 200 to 300° C., sometimes up to 500° C.

According to the invention, the hot product gas mixture is cooled by direct cooling in a quench apparatus 1 to a temperature of generally from 100 to 180° C. before, advantageously from an application point of view together with the quench liquid 1 used, it is passed into a condensation column comprising separating internals, preferably into the lower section (preferably the lowermost, for example the bottom space), for the purposes of fractional condensation.

Useful condensation column internals include in principle all common internals, in particular trays, structured packings and/or random packings. Among the trays, preference is given to bubble-cap trays, sieve trays, valve trays and/or dual-flow trays. Typically, the total number of separating trays in a tray column is from 20 to 100, frequently from 20 to 80 and preferably from 50 to 80.

According to the invention, the condensation column is preferably one whose separating internals from bottom to top are initially dual-flow trays followed by hydraulically sealed crossflow trays (e.g. Thormann® trays), as recommended by DE-A 19924532 and DE-A 10243625. The number of dual-flow trays may be from 5 to 60, frequently from 25 to 45, and the number of the hydraulically sealed crossflow trays may likewise be from 5 to 60, frequently from 30 to 50. When the acid water quench (quench 3) is integrated into the condensation column, preferred separating internals for this region of the condensation column (acrylic acid content of the reflux liquid viewed from bottom to top generally $\leq 10$% by weight) are valve trays, as described by DE-A 19924532 and DE-A 10243625. However, other common separating internals could also be used in principle.

Useful quench apparatus 1 includes all apparatus known from the prior art for this purpose (e.g. spray scrubbers, Venturi scrubbers, bubble columns or other apparatus having sprayed surfaces), although preference is given to using Venturi scrubbers or spray coolers.

For indirect cooling or heating of the quench liquid 1, in particular on startup, preference is given to conducting it through a heat transferor or heat exchanger. In this regard, all common heat transferors or heat exchangers are suitable. Preference is given to tube bundle heat exchangers, plate heat exchangers and air coolers. Suitable cooling media are air in the case of corresponding air coolers and cooling liquids, especially water, in the case of the other cooling apparatus.

According to the invention, the quench liquid 1 used may be, for example, bottom liquid containing acrylic acid oligomers from the bottom of the condensation column, or high boiler fraction containing acrylic acid oligomers via a sidestream takeoff disposed in the vicinity of the bottom, or, with preference according to the invention, a mixture of such bottom liquid containing acrylic acid oligomers and high boiler fraction. Preference is given to conducting only the proportion of the quench liquid 1 removed from the bottom of the condensation column via the abovementioned heat exchanger. According to the invention, the temperature of the quench liquid 1 on entry into the quench apparatus 1 is advantageously generally from 90° C. to 120° C.

The introduction point for the quenched product gas mixture of the catalytic gas phase partial oxidation, with preference according to the invention in a mixture with the quench liquid 1 used for direct cooling, into the condensation column is advantageously disposed in the bottom space of this column which advantageously contains an integrated centrifugal drop separator and is generally separated from the lowermost separating internal by a first chimney tray. In the particularly preferred embodiment of the condensation column and of the process according to the invention which are described exclusively hereinbelow, the first separating internal is the first dual-flow tray of a first series of advantageously equidistantly arranged dual-flow trays. The chimney tray functions at the same time as a collecting tray from which condensate (high boiler fraction containing acrylic acid oligomers) is continuously withdrawn and conducted into the quench apparatus 1 as a portion of the quench liquid 1. The first series of dual-flow trays is completed by a second chimney tray (collecting tray). From this second collecting tray, crude acrylic acid is continuously withdrawn from the sidestream takeoff as a middle boiler fraction which normally has a purity of ≧90 or ≧95% by weight.

Advantageously, this crude acrylic acid will be fed to further distillative (rectificative) and/or crystallizative further purification stages and at least a portion of the bottom liquids and/or mother liquors occurring in this distillation (rectification) and/or crystallization will be recycled into the condensation column below the second but above the first collecting tray. This recycling is preferably thermally integrated. In other words, the cold mother liquor to be recycled is used via one or more indirect heat exchange stages connected in series, in order to cool the crude acrylic acid withdrawn from the condensation column and to be further purified crystallizatively. At the same time, this heats the mother liquor.

Advantageously, the crude acrylic acid withdrawn as the middle boiler fraction will be fed to a crystallization for the purpose of further purification. The crystallization process to be used is in principle subject to no restriction. The crystallization may be carried out continuously or batchwise, in one or more stages, to any desired degrees of purity.

If required, water may have been added in advance of the crystallization to the crude acrylic acid to be purified crystallizatively (in general, this then contains, based on the amount of acrylic acid present, up to 10% by weight, usually up to 5% by weight, of water). In the case of increased aldehyde or other secondary component contents, water addition may be dispensed with, since the aldehydes in this case are able to assume the function of the water.

It is surprising that esterification-grade acrylic acid (e.g. for the preparation of n-butyl acrylate, 2-ethylhexyl acrylate, methyl acrylate and ethyl acrylate) (purity ≧98% by weight) can be obtained by only a single crystallization stage. Advantageously, this crystallization stage is performed as a suspension crystallization, as described in column 10 of DE-A 19924532 or in example 1 of DE-A 10223058. The acrylic acid crystals resulting from the suspension crystallization have a cubic to cuboidal appearance. The length (L) to thickness (T) ratio is typically in the range from L:T=1:1 to L:T=6:1, preferably in the range from 1:1 to 4:1, and more preferably in the range from 1.5:1 to 3.5:1. The thickness T of the crystals is typically in the range from 20 to 600 $\mu$m, often from 50 to 300 $\mu$m. The length L of the crystals is typically in the range from 50 to 1500 $\mu$m, often from 200 to 800 $\mu$m. In the case of esterification-grade acrylic acid, the suspension crystals may be removed from the remaining mother liquor on a centrifuge (e.g. a 2- or 3-stage pusher centrifuge), and the crystals removed are advantageously washed on the centrifuge using molten pure crystals. When the suspension crystals are removed from the remaining mother liquor by means of a melt-washing column (for example one according to WO 01/77056, or DE-A 10156016, or DE-A 10223058), it is even possible to obtain superabsorbent-grade acrylic acid (purity ≧99.7% by weight) by means of a single crystallization stage, i.e. acrylic acid which is suitable for preparing water-superabsorbent or other polyacrylates. In this case, the entirety of the mother liquor removed is advantageously recycled into the separating column according to the invention.

However, the crystallization may also be carried out as a fractional falling-film crystallization, as recommended by EP-A 616998. This may encompass, for example, three or more (e.g. 3 to 4) purification stages (falling-film crystallizers suitable in this context may contain, for example, from 1000 to 1400 crystallization tubes of length from 10 to 15 m and an external diameter from 50 to 100 mm). The mother liquor removed in a higher purification stage may be recycled into one of the preceding purification stages. The mother liquor removed in the first purification stage is advantageously recycled completely into the condensation column. Alternatively to the recycling into one of the preceding purification stages, the mother liquors of the individual purification stages may also be recycled in their entirety into the condensation column. The pure product of the penultimate purification stage may be recycled completely or only partially to the last purification stage. When only a portion is fed, the remaining amount will generally be admixed with the pure product of the last purification stage to give the ready-for-use end product.

According to the invention, a portion of the crude acrylic acid withdrawn from the second collecting tray will advantageously be fed to the dual-flow tray disposed below this collecting tray. Any mother liquor to be recycled into the condensation column will generally also be fed to this tray. Before it is fed, the mother liquor will generally, as already described, be heated in a thermally integrated system to a temperature which approximately corresponds to the withdrawal temperature of the crude acrylic acid.

Another portion of the crude acrylic acid withdrawn from the second collecting tray will be heated by from 10 to 15° C. by indirect heat exchange and be recycled into the condensation column above the takeoff point, preferably immediately below the first following dual-flow tray. This measure has a beneficial effect on the acetic acid content of the crude acrylic acid removed.

Above the second collecting tray there initially follows a second series of advantageously equidistant dual-flow trays which are then succeeded by hydraulically sealed crossflow mass transfer trays (e.g. Thormann trays or modified Thormann trays according to DE-A 10243625) which are advantageously likewise arranged equidistantly. The uppermost dual-flow tray is frequently equipped as a distributor tray. In other words, it has, for example, overflow channels having serrated overflows.

The crossflow mass transfer trays are completed by a third chimney tray (collecting tray).

Above the third collecting tray are disposed valve trays-which preferably have double flow. The principle of valve trays and also of valve trays which can be used according to the invention can be found, for example, in Technische Fortschrittsberichte [Technical Progress Reports], volume 61, Grundlagen der Dimensionierung von Kolonnenböden [The Basics of Dimensioning Column Trays], p. 96 to 138. They are characterized substantially in that they provide a flow orifice to the vapor flowing through which corresponds to the particular loading over a wide range of loadings. According to the invention, preference is given to using ballast trays. In other words, in the orifices of the tray are disposed cages having orifices closed by weights. Particular preference is given according to the invention to VV12 valves from Stahl, DE, Viernheim. In the valve tray space, substantially water and constituents less volatile than water condense. The condensate obtained is referred to as acid water.

Acid water is continuously removed from the third collecting tray. A portion of the water removed is recycled into the condensation column at the uppermost of the crossflow mass transfer trays. Another portion of the acid water removed is cooled by indirect heat exchange and, advantageously divided, likewise recycled into the condensation column. A portion is recycled to the uppermost valve tray (at a temperature of from 15 to 25° C., preferably from 20 to 25° C.) and the other portion is recycled into the separating column according to the invention at a valve tray disposed approximately centrally between the third collecting tray and the uppermost valve tray (at a temperature of from 20 to 35° C., preferably from 25 to 30° C.).

Some of the cooling is effected by conducting the acid water through the evaporator of the $C_3$ precursor (e.g. the propylene evaporator), in order to convert $C_3$ precursors, e.g. propylene, stored in the liquid state to the gas phase for the heterogeneously catalyzed gas phase oxidation.

Constituents more volatile than water are removed in gaseous form at the top of the separating column according to the invention and normally at least partially recycled as diluent gas into the gas phase oxidation. In order to avoid condensation in the cycle gas compressor, the offgas is overheated beforehand by indirect heat exchange. The portion of the offgas which is not recycled is normally incinerated. A portion of the cycle gas is, as already described, advantageously used as support gas in the dissociation of the acrylic acid oligomers.

For the purpose of polymerization inhibition, a solution of p-methoxyphenol (=MEHQ) in acrylic acid and optionally in addition a solution of phenothiazine in acrylic acid are fed to the uppermost of the hydraulically sealed crossflow mass transfer trays. The acrylic acid used is preferably pure acrylic acid, as obtained in the further purification of the crude acrylic acid removed. For example, the glacial acrylic acid (pure product) obtained in the crystallizative further purification may be used.

This solution is advantageously used for pure product stabilization.

In addition, a solution of phenothiazine (=PTZ) in pure product is fed approximately in the middle of the column section having the hydraulically sealed crossflow mass transfer trays.

In principle, the acid water formation may also be practiced outside the condensation column. In this case, substantially water will be advantageously condensed out of the low boiler gas stream which then leaves the top of the condensation column by direct cooling in a space free of internals or containing internals using a quench liquid 3. The resulting condensate is in turn the acid water. It is then sensible to recycle a portion of the acid water into the condensation column to increase the separating performance at the top. A further portion of the acid water is advantageously discharged and disposed of (e.g. incinerated) and the remaining portion of the acid water is customarily cooled indirectly in an external heat exchanger and used as the quench liquid 3. Constituents of the low boiler stream which are more volatile than water again form offgas which is normally at least partly recycled into the gas phase oxidation as cycle gas or used in the dissociation.

In the preferred variant of the process according to the invention, the dual-flow trays in the condensation column advantageously extend to about the cross section in the condensation column from which the acrylic acid contents of the reflux liquid viewed toward the top of the column are $\leq 90\%$ by weight, based on the weight of the reflux liquid.

The number of dual-flow trays for the preferred variant of the process according to the invention is, as already stated, generally from 25 to 45. Its orifice ratio is advantageously from 15 to 25%. The passages of the dual-flow trays are preferably circular holes having a uniform circle diameter. The latter is advantageously from 10 to 20 mm. If required, the hole diameter in the condensation column may be decreased or increased and/or the number of holes may be decreased or increased from top to bottom (for example, the hole diameter may be a uniform 14 mm and the orifice ratio may increase from top to bottom from 17.4% to 18.3%). However, the number of holes may also be constant over all dual-flow trays. Preference is also given to the circular holes being uniformly distributed over the individual dual-flow trays in strict triangular pitch (cf. DE-A 10230219).

Also, the punched burr of the passages punched out of the dual-flow trays preferably points downward in the condensation column (this reduces undesired polymer formation).

According to the invention, it is sensible when the number of dual-flow trays used in the condensation column corresponds to from about 10 to 15 theoretical plates.

The number of the hydraulically sealed crossflow trays which follows the dual-flow trays in the condensation column preferred according to the invention is, as already mentioned, generally from 30 to 50. Its orifice ratio will advantageously be from 5 to 25%, preferably from 10 to 20% (the orifice ratio quite generally represents the percentage of the passage cross sections in the total cross section; in the case of the crossflow mass transfer trays to be used with preference, it is quite generally advantageously within the abovementioned range).

According to the invention, preference is given to using single flow crossflow mass transfer trays.

In general, the number of hydraulically sealed crossflow trays for the preferred variant of the process according to the invention is such that it corresponds to from about 10 to 30, frequently 25, theoretical plates.

Both the hydraulically sealed crossflow trays and also any valve trays used have at least one downcomer. They may both either have a single-flow or multi-flow configuration, for example double-flow. In the case of the single-flow configuration, they may have more than one downcomer. In general, the upcomers of the valve trays are also hydraulically sealed.

The polymerization inhibition of the quench system 1 for the product gas mixture of the partial gas phase oxidation may be achieved either using polymerization inhibitors contained in the bottom liquid used for quenching or using polymerization inhibitors contained in high boiler fraction used for quenching.

The advantage of the process according to the invention is once again based on the fact that when the yield is the same, it results in an increased purity of the crude acrylic acid (and therefore all subsequent purification stages thereof), or, when the purity is the same, results in an increased yield of crude acrylic acid (and therefore all subsequent purification stages thereof). All of the statements made in this document apply especially to a product gas mixture which has been obtained by heterogeneous partial oxidation of propylene to acrylic acid. The preferred embodiment of the process according to the invention described hereinabove does not in any way restrict its general performability.

For example, it may also be carried out as illustrated in FIG. 2 of DE-A 19924533 or as described in DE-A 10235847, although with the difference that the dissociation gases are subjected to a countercurrent rectification before their recycling.

EXAMPLE AND COMPARATIVE EXAMPLE

Example 1

The Steady State is Described

From a heterogeneously catalyzed gas phase oxidation of propylene of "polymer grade" purity, a product gas mixture at a temperature of 270° C. was obtained and had the following composition:

11.8201% by weight of acrylic acid,
0.2685% by weight of acetic acid,
5.2103% by weight of water,
0.0279% by weight of formic acid,
0.0989% by weight of formaldehyde,
0.1472% by weight of acrolein,
0.0028% by weight of propionic acid,
0.0033% by weight of furfurals,
0.0014% by weight of allyl acrylate,
0.0005% by weight of allyl formate,
0.0038% by weight of benzaldehyde,
0.1352% by weight of maleic anhydride,
0.0113% by weight of benzoic acid,
0.0147% by weight of phthalic anhydride,
1.8042% by weight of $CO_2$,
0.5898% by weight of CO,
0.5519% by weight of propane,
0.2693% by weight of propylene,
4.0253% by weight of $O_2$, and
75.0145% by weight of $N_2$.
Further components were not detected.

The product gas mixture (170 855 kg/h) is cooled in a spray cooler operated in cocurrent (quench 1) by direct cooling to a temperature of 113.2° C.

The liquid used for direct cooling (quench liquid 1) is a mixture of bottom liquid which is removed from the bottom of the condensation column described hereinbelow, and of high boiler fraction which is removed from the first collecting tray which completes the bottom space of this condensation column.

The composition of the bottom liquid is:
41.0698% by weight of acrylic acid,
0.2047% by weight of acetic acid,
0.8436% by weight of water,
0.0094% by weight of formic acid,
0.0009% by weight of formaldehyde,
0.0116% by weight of acrolein,
0.0231% by weight of propionic acid,
0.2317% by weight of furfurals,
0.0011% by weight of allyl acrylate,
0.0001% by weight of allyl formate,
0.2506% by weight of benzaldehyde,
6.1970% by weight of maleic anhydride,
0.7396% by weight of benzoic acid,
0.9658% by weight of phthalic anhydride,
21.0855% by weight of diacrylic acid,
24.4047% by weight of polyacrylic acid (Michael adducts),
0.4886% by weight of phenothiazine,
0.6618% by weight of MEHQ,
0.0819% by weight of other high-boiling constituents, and
0.0002% by weight of oxygen.

The high boiler fraction has the following composition:
91.6313% by weight of acrylic acid,
0.3777% by weight of acetic acid,
1.4924% by weight of water,
0.0145% by weight of formic acid,
0.0016% by weight of formaldehyde,
0.0108% by weight of acrolein,
0.0528% by weight of propionic acid,
0.4322% by weight of furfurals,
0.0025% by weight of allyl acrylate,
0.0003% by weight of allyl formate,
0.3321% by weight of benzaldehyde,
4.4666% by weight of maleic anhydride,
0.0193% by weight of benzoic acid,
0.0169% by weight of phthalic anhydride,
1.0767% by weight of diacrylic acid,
0.0175% by weight of phenothiazine,
0.0544% by weight of MEHQ, and
0.0004% by weight of oxygen.

The amount of high boiler fraction removed is 72 629 kg/h. It is removed at a temperature of 99.5° C. and fed at this temperature to the spray cooler (quench 1). The amount of bottom liquid removed from the condensation column is 249 816 kg/h. It is withdrawn at a temperature of 110.8° C. Only an amount of 247 216 kg/h is fed to the spray cooler at this temperature. 2300 kg/h are fed to the dissociation and 300 kg/h are fed to the quench circuit 2, in order to inhibit this against undesired polymerization.

The mixture of product gas mixture and quench liquid 1 cooled to 113.2° C. resulting from the direct cooling is conducted as such into the bottom of the condensation column. The pressure in the bottom space and in the quench 1 is 1.48 bar. The height of the condensation column is 54.3 m.

The internal diameter of the condensation column in the region of the Thormann trays is 6.5 m and otherwise 6.0 m.

2300 kg/h of the bottom liquid removed are fed to a dissociation apparatus consisting of a forced circulation-decompression evaporator and a dual-flow tray rectification column attached seamlessly thereto. The number of dual-flow trays is 50. Like the condensation column, the rectification column is insulated from the environment. The internal diameter of the rectification column over all dual-flow trays is a uniform 2.4 m. Its height is 27 m. The dual-flow trays are arranged equidistantly (400 mm) in the rectification column. Their orifice ratio is a uniform 12%. Viewed from bottom to top, the hole diameter of the first eight dual-flow trays is a uniform 25 mm (hole arrangement correspondingly strict triangular pitch) and the hole diameter of all subsequent dual-flow trays is a uniform 14 mm (hole arrangement likewise correspondingly strict triangular pitch). The bottom liquid to be subjected to dissociation is fed to the eighth dual-flow tray (from below).

25 481 kg/h of cycle gas removed at the top of the condensation column, then overheated and compressed is fed (as support gas) into the forced circulation evaporator (pressure=2.9 bar; temperature: 160° C.).

The composition of the cycle gas is:

0.2651% by weight of acrylic acid,
0.0989% by weight of acetic acid,
2.9333% by weight of water,
0.0059% by weight of formic acid,
0.1720% by weight of acrolein,
0.0002% by weight of propionic acid,
0.0002% by weight of furfurals,
0.0013% by weight of allyl formate,
4.7235% by weight of oxygen,
2.1171% by weight of $CO_2$,
0.6921% by weight of CO,
0.6466% by weight of propane,
0.3161% by weight of propylene and
88.0277% by weight of nitrogen.

558 028 kg/h of liquid phase are continually withdrawn at a temperature of 156.5° C. from the forced circulation-decompression evaporator. 557 457 kg/h thereof are recycled at a temperature of 161.5° C. into the forced circulation-decompression evaporator.

The other 571 kg/h thereof are degassed and, diluted with methanol, fed to residue incineration.

The dissociation gases formed in the forced circulation-decompression evaporator are conveyed by the fed support gas into the attached rectification column and rise into reflux liquid falling therein.

A gas mixture (comprising recycle gas and dissociation gas) is conducted out of the top of the rectification column in an amount of 39 514 kg/h (temp.=94.4° C., pressure=1.60 bar) and cooled by direct cooling to a temperature of 59.9° C. and partially condensed in a spray cooler operated in cocurrent (quench 2).

The gas mixture remaining after the direct cooling in an amount of 27 510 kg/h and having the following composition is recycled into the bottom space of the condensation column (not immersed):

7.5140% by weight of acrylic acid,
0.1106% by weight of acetic acid,
2.7934% by weight of water,
0.0064% by weight of formic acid,
0.0001% by weight of formaldehyde,
0.1603% by weight of acrolein,
0.0024% by weight of propionic acid,
0.0034% by weight of furfurals,
0.0001% by weight of allyl acrylate,
0.0012% by weight of allyl formate,
0.0003% by weight of benzaldehyde,
0.0041% by weight of maleic anhydride,
4.3751% by weight of oxygen,
1.9610% by weight of $CO_2$,
0.6411% by weight of CO,
0.5989% by weight of propane,
0.2928% by weight of propylene and
81.5349% by weight of nitrogen.

The quench liquid 2 used is a mixture of 300 kg/h of the bottom liquid removed from the bottom of the condensation column and condensate formed in the quench 2 in the direct cooling. 128 713 kg/h of this mixture are cooled to 32° C. by indirect cooling and atomized in the spray cooler 2. 12 304 kg/h of the same mixture are recycled as reflux liquid at a temperature of 59.9° C. to the uppermost dual-flow tray of the rectification column.

The composition of the quench liquid 2 is:

92.9743% by weight of acrylic acid,
0.6443% by weight of acetic acid,
4.7794% by weight of water,
0.0204% by weight of formic acid,
0.0356% by weight of acrolein,
0.0294% by weight of propionic acid,
0.0506% by weight of furfurals,
0.0007% by weight of allyl acrylate,
0.0020% by weight of allyl formate,
0.0093% by weight of benzaldehyde,
0.2050% by weight of maleic anhydride,
0.0181% by weight of benzoic acid,
0.0236% by weight of phthalic anhydride,
0.5143% by weight of diacrylic acid,
0.5950% by weight of polyacrylic acid (Michael adducts),
0.0119% by weight of phenothiazine,
0.0163% by weight of MEHQ,
0.0685% by weight of other high-boiling constituents, and
0.0012% by weight of oxygen.

A centrifugal drop separator is integrated into the bottom space of the condensation column and prevents droplets of the bottom liquid being entrained upward out of the bottom space.

As already mentioned, the bottom space of the condensation column is completed at a column height (like all column heights, calculated from the column bottom) of 7.80 m by a first collecting tray (chimney tray having 16 approximately uniformly distributed roofed chimneys; chimney diameter: 600 mm; chimney height: 1 m).

The collecting tray is configured with a double wall having 2° gradients toward the interior and with a central takeoff cup and takeoff nozzle (DN~200). The free gas cross section is approx. 30%.

As already mentioned, 72 629 kg/h of liquid are removed from this first collecting tray and conducted into the spray cooler 1.

The bottom temperature is 110.8° C. The pressure is 1.48 bar.

2.0 m above the first collecting tray is disposed the first of initially 15 dual-flow trays. These dual-flow trays (hole diameter a uniform 14 mm, number of holes a uniform 33 678, orifice ratio a uniform 18%) are mounted equidistantly at a tray separation of 380 mm. The passages consist of circular orifices of a uniform diameter of 14 mm whose punched burr points downward in the separation column. The orifice ratio is approx. 20%. The arrangement of the centers of the passage circles follows a strict triangular pitch. The separation of two neighboring circle centers is 30 mm.

The fifteenth dual-flow tray is configured as a distributor tray. For this purpose, it comprises two inserted tubes (DN~150) having 40 outlet drillholes (diameter: 15 mm) per inserted tube.

The first series of dual-flow trays is completed by a second collecting tray (chimney tray having 16 approx. uniformly distributed roofed chimneys; chimney height approx. 1.70 m, central takeoff cup having takeoff nozzles (DN~250), free gas cross section of ~30%) which is mounted 1.50 m above the last dual-flow tray.

Crude acrylic acid is continuously removed at 1.47 bar from this second collecting tray at a temperature of 100.6° C. and has the following composition:

96.9126% by weight of acrylic acid,
0.4500% by weight of acetic acid,
1.5250% by weight of water,
0.0137% by weight of formic acid,
0.0015% by weight of formaldehyde,
0.0088% by weight of acrolein,
0.0638% by weight of propionic acid,
0.2000% by weight of furfurals,
0.0027% by weight of allyl acrylate,
0.0003% by weight of allyl formate,
0.0467% by weight of benzaldehyde,
0.2164% by weight of maleic anhydride,
0.5281% by weight of diacrylic acid,
0.0120% by weight of phenothiazine,
0.0180% by weight of MEHQ, and
0.0004% by weight of oxygen.

455 993 kg/h of the crude acrylic acid removed from the second collecting tray are heated by indirect heat exchange to 110.6° C. and recycled immediately below the dual-flow tray immediately following the second collecting tray in the upward direction in the condensation column.

91 045 kg/h of the crude acrylic acid removed from the second collecting tray are cooled to a temperature of 29° C. in a plurality of stages by indirect heat exchange (preferably thermally integrated against the mother liquor to be recycled into the condensation column). 1099 kg/h of water are then added to the cooled crude acrylic acid. The resulting mixture is cooled again to 20° C. by repeated indirect heat exchange and then conducted into from two to three cooling disk crystallizers. These are each a trough in which from 20 to 24 wiped circular cooling plates (which are flowed through internally by a cooling medium (mixture of water and glycol; proportion of glycol=10 to 50% by weight, preferably 25 to 35% by weight)) are arranged hanging in succession at an equidistant separation of from 20 to 40 cm (plate diameter typically from 2 to 4 m, preferably from 2.5 to 3 m). The cooling medium is conveyed in countercurrent to the crystallizing mixture through the crystallizer from cooling disk to cooling disk. However, it may also be conducted over the cooling plates divided into 2 or 3 parallel streams. The entrance temperature of the cooling medium (the brine) is from −2 to +5° C. The exit temperature is from 2 to 7° C. higher. The wiping of the cooling plates suppresses the formation of a crystal layer. The crude acrylic acid having increased water content is conducted continuously (pumped or controlled by overflows) from back to front through the crystallizer. The monophasic crude acrylic acid having increased water content thickens (residence time from 0.5 to 4 h, preferably from 1.5 to 2.5 h) to a biphasic suspension comprising acrylic acid crystals as the solid phase and having a temperature of from 6 to 11° C. and a solids content at the exit of from 20 to 35% by weight. The speed of the wiper is from 2 to 15 revolutions per minute, preferably from 4 to 10 revolutions per minute. The shaft which drives the wipers and passes through the centers of the cooling disks is sealed with water-washed stuffing box packings (packing braids made of Teflon or graphite).

On the circumference of the cooling disks where it is not possible to wipe, a hollow profile (e.g. in the simplest embodiment a tube) is mounted (e.g. welded on) and is heated by means of a second heat carrier (e.g. likewise water/glycol mixture) (to a temperature above the crystallization temperature; usually within the temperature range from 8 to 20° C., preferably from 10 to 14° C.). These circumference heaters are flowed through in parallel by the second heat carrier.

Furthermore, the wipers are preferably segmented in the radial direction ($\geq 2$, $\leq 6$ segments in general). The specific pressing force of the wipers perpendicular to the cooling surface in the installed state is from 1 to 10 N, preferably from 3 to 5 N, per cm of active wiping edge length. In addition to the wipers, the shaft drives paddles (there are advantageously two each in a symmetrical arrangement between two cooling disks and before the first and last cooling disk) which effect improved mixing.

In the last section of the crystallizer in the conveying direction of the suspension (preferably beyond the last cooling disk), the suspension is conducted via an attached tube (advantageously mounted in an immersed manner; alternatively, the suspension may flow via an overflow wier into a stirred reservoir, whence the washing columns are charged) to hydraulic melt-washing columns, as described in DE-A 10156016 and DE-A 10223058, in order to separate the mother liquor from the suspension crystals. The washing column is charged with crystal suspension by means of a centrifugal pump or a rotary piston pump. The control stream pump is likewise embodied by a rotary piston pump or by a centrifugal pump having a regulating valve. The pressure at the lower end of a washing column is typically $\geq 100$ mbar and $\leq 5$ bar lower than the pressure at the top of the washing column. The top pressure is generally up to 6 bar, usually from 0.5 to 4 bar. The blade speed is usually at values of >0 and $\leq 100$/min, or $\leq 60$/min. The temperature in the melt circuit is normally from 13 to 16° C. The filtration front is detected according to DE-A 10036880 by from 2 to 4 optical sensors. The washing front is controlled by means of temperature measurement in the crystal bed.

The total height of the crystal bed is typically from 300 to 1500 mm, usually from 400 to 1000 mm. The washing front is typically from 10 to 400 mm, usually from 20 to 250 mm, above the blade. Useful melt circuit pumps are a centrifugal pump with product-side washing of the shaft seal (slip-ring seal) or a magnet-coupled pump with increased washing of the sliding bearings. The circulation amount in the melt circuit is from 2 to 30 m³/h, usually from 5 to 20 m³/h, per metric tonne of purified crystals removed with the blade. The melt circuit is stabilized by means of from 100 to 300 ppm by weight of MEHQ. In addition, air is introduced into the melt circuit and its excess (=the proportion not dissolved in the wash melt) is removed by a gas separator before entry of the wash melt into the washing column

[a] to prepare esterification-grade acrylic acid, it is sufficient to carry out the removal of the suspension crystals by means of a centrifuge (e.g. a 2- or 3-stage pressure centrifuge) instead of a melt-washing column. Suitable screen gap widths are from 150 to 300 μm; centrifugal accelerations which can be used are from 500 to 900 g, usually from 600 to 800 g; suitable stroke rates are from 40 to 80 strokes/min.

Preference is given to washing the crystals removed from the 2nd or 3rd stage of the centrifuge with from 0.15 to 0.3 kg of washing liquid per kg of crystals. The temperature of the washing liquid is from 15 to 30° C., preferably from 20 to 30° C. To avoid deposits, the solids discharge chute of the centrifuge is flushed with flushing liquid heated to from 15 to 30° C. Flushing and washing liquid are preferably molten crystals removed and washed by the centrifuge. To avoid deposits and encrustations, it is advantageous to heat the centrifuge housing, the suspension feed tube and the washing liquid feed tube to a temperature $\geq 15°$ C. and $\leq 40°$ C. The product space of the centrifuge is advantageously inertized with nitrogen or with a mixture of air and nitrogen. The shaft seal is purged with gas (e.g. nitrogen or a mixture of air and nitrogen) or with water.

b) Alternatively to the suspension crystallization, it is also possible to use a layer crystallization (e.g. falling-film crystallization according to EP-A 616998 or tube with full flow-through) having 3 or more (e.g. 3 to 4) purification stages. Instead of recycling the mother liquor from a following purification stage into a preceding purification stage, it is also possible to recycle them together into the condensation column.]

From the melt circuits which are stabilized by the addition of 3 kg/h of MEHQ, 19 584 kg/h of glacial acrylic acid of the following composition are removed:

99.8360% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid, and 0.0150% by weight of MEHQ.

It is outstandingly suitable for preparing superabsorbents based on poly-sodium acrylate.

13 kg/h of PTZ are dissolved in 834 kg/h of glacial acrylic acid for preparing an inhibitor solution 1. 19 kg/h of MEHQ are dissolved in 30 kg/h of inhibitor solution 1 to form the inhibitor solution 2.

The mother liquor removed in the washing columns is initially fed into a heatable reservoir and from there into a tank. From this tank, it is recycled heated to 90° C. in an amount of 72 564 kg/h to the fifteenth dual-flow tray of the condensation column (counted from below). The composition of this recycled mother liquor is as follows:

94.6506% by weight of acrylic acid, 0.0539% by weight of acetic acid, 3.4196% by weight of water, 0.0172% by weight of formic acid, 0.0018% by weight of formaldehyde, 0.0111% by weight of acrolein, 0.0746% by weight of propionic acid, 0.2509% by weight of furfurals, 0.0034% by weight of allyl acrylate, 0.0003% by weight of allyl formate, 0.0586% by weight of benzaldehyde, 0.2715% by weight of maleic anhydride, 0.6625% by weight of diacrylic acid, 0.0151% by weight of phenothiazine, 0.0233% by weight of MEHQ, and 0.0005% by weight of oxygen.

2.9 m above the second collecting tray in the condensation column is disposed the first of 21 further dual-flow trays of the type already described (hole diameter again a uniform 14 mm, but number of holes a uniform 32 020 and orifice ratio a uniform 17.4%) which were again arranged equidistantly at a tray separation of 380 mm. The last of these 21 dual-flow trays is configured as a distributor tray with overflow channels having a serrated overflow.

800 mm above the last dual-flow tray, the condensation column begins to widen in a conical manner. 500 mm above the last dual-flow tray, this widening ends at an internal column diameter of 6.50 m.

At this height, i.e. 1.50 m above the last dual-flow tray, begins an equidistant (tray separation=500 mm) arrangement of 28 conventional, single-flow Thormann trays. The Thormann trays are configured in such a way that the arrangement of the transport slots in the hoods of the Thormann trays in successive channels in the crossflow direction each generate a mutually opposed flow direction of the liquid.

The orifice ratio of the Thormann trays is 14%. The ratio of chimney surface area to slot exit surface area is 0.8. The chimney height and the height of the overflow weir are 40 mm. The bottom clearance of the bubble-cap (separation between lower edge of slot and tray) is 10 mm. The slot height is 15 mm. The angle between the obliquely angled slot and longitudinal edge of the hood is 30 degrees. The maximum length of the longitudinal edge of the hood is 800 mm. In the peripheral region of the column, the hood length reduces down to 200 mm for reasons of adaptation to the roundness of the column. The separation between two hoods disposed on one line in the crossflow direction is 66 mm. The drain surface area of the downcomer is 1.5%, based on the cross-sectional area of the tray. The width between the two longitudinal edges of a hood is 64 mm.

At the height of the uppermost Thormann tray, the separating column begins to narrow again in a conical manner. 700 mm above the uppermost Thormann trays, this narrowing is complete and the column diameter has contracted again to 6.00 m.

1.70 m above the uppermost Thormann trays is disposed the third collecting tray (chimney tray having 16 approx. uniformly distributed roofed chimneys, chimney height= 1.50 m).

From the third collecting tray, 533 818 kg/h of acid water at a temperature of 68.6° C. and a pressure of 1.24 bar are removed.

The composition of the acid water is:

11.8864% by weight of acrylic acid, 4.1983% by weight of acetic acid, 80.6473% by weight of water, 0.5365% by weight of formic acid, 2.3900% by weight of formaldehyde, 0.0153% by weight of acrolein, 0.0092% by weight of propionic acid, 0.0016% by weight of furfurals, 0.0132% by weight of allyl formate, and 0.0001% by weight of MEHQ.

29 443 kg/h of the acid water withdrawn (68.6° C.) are recycled together with the inhibitor solution 2 to the uppermost Thormann tray.

817 kg/h of the inhibitor solution 1 are recycled (at a temperature of 25° C. and a pressure of 1.10 bar) to the 19th Thormann tray (viewed from below).

7071 kg/h of the acid water removed are fed to incineration.

298 383 kg/h of the acid water removed are recycled at a temperature of 29° C. to the sixth of the valve trays to be described hereinbelow (counted from below).

198 922 kg/h of the acid water removed are recycled at a temperature of 22.5° C. to the uppermost of the valve trays to be described hereinbelow.

2300 mm above the third collecting tray, 11 double-flow valve trays are mounted in equidistant arrangement (tray separation=500 mm) in the condensation column. The height of the drain weir is 35 mm. The orifice ratio is 18% and the sum of the drain surface areas of the downcomers of two successive valve trays is 10% of the column cross-sectional area. The valves used were VV12 valves from Stahl, DE, Viernheim.

The pressure at the top of the column is 1.2 bar. At the top of the column, 171 078 kg/h of offgas leave the separating column at a temperature of 35.2° C. and have the following composition:

0.2651% by weight of acrylic acid,
0.0989% by weight of acetic acid,
2.9333% by weight of water,
0.0059% by weight of formic acid,
0.1720% by weight of acrolein,
0.0002% by weight of propionic acid,
0.0002% by weight of furfurals,
0.0013% by weight of allyl formate,
2.1171% by weight of $CO_2$,
0.6921% by weight of CO,
0.6466% by weight of propane,
0.3161% by weight of propylene
4.7235% by weight of $O_2$, and
88.0277% by weight of $N_2$.

In an indirect heat exchanger, the offgas is heated to 38° C. and 96 984 kg/h of this offgas are subsequently conducted via a cycle gas compressor as diluent gas into the gas phase oxidation and into the dissociation, and 47 094 kg/h of the offgas are fed to incineration.

2. Comparative Example

Like the example, except that no reflux liquid is conducted to the top of the rectification column, i.e. the quench circuit 2 is closed and the mixture of dissociation gas and cycle gas flowing through the rectification column in gaseous form is passed directly into the bottom of the condensation column. The cycle gas amount is reduced to 3900 kg/h, in order to maintain the dissociation temperature of 161.5° C. The amount of water is increased to 1390 kg/h, in order to maintain the water content in the feed to the suspension crystallization.

At the same amounts, the purity of crude acrylic acid withdrawn via the sidestream takeoff and glacial acrylic acid removed in the washing column changed to the following specifications:

Crude acrylic acid:
90.8894% by weight of acrylic acid,
0.4500% by weight of acetic acid,
1.2067% by weight of water,
0.0133% by weight of formic acid,
0.0015% by weight of formaldehyde,
0.0093% by weight of acrolein,
0.0649% by weight of propionic acid,
2.9306% by weight of furfurals,
0.0027% by weight of allyl acrylate,
0.0001% by weight of allyl formate,
3.2064% by weight of benzaldehyde,
0.5816% by weight of maleic anhydride,
0.6131% by weight of diacrylic acid,
0.0120% by weight of phenothiazine,
0.0180% by weight of MEHQ, and
0.0003% by weight of oxygen.

Glacial acrylic acid:
99.8331% by weight of acrylic acid,
0.0947% by weight of acetic acid,
0.0332% by weight of water,
0.0206% by weight of propionic acid,
0.0014% by weight of furfurals,
0.0003% by weight of maleic anhydride,
0.0003% by weight of diacrylic acid,
0.0150% by weight of MEHQ, and
0.0015% by weight of benzaldehyde.

We claim:

1. A process for preparing acrylic acid by generating an acrylic acid-containing product gas mixture by heterogeneously catalyzed gas phase partial oxidation of at least one $C_3$ precursor of acrylic acid with molecular oxygen over catalysts in the solid state at elevated temperature, initially reducing the temperature of a hot acrylic acid-containing product gas mixture by direct cooling with a quench liquid 1 and subsequently passing the cooled product gas mixture which may possibly contain portions of evaporated quench liquid 1 into a condensation column equipped with separating internals, allowing said product gas mixture to rise within the condensation column, thus fractionally condensing it, and withdrawing crude acrylic acid as the target product from the condensation column in a sidestream and withdrawing bottom liquid comprising acrylic acid oligomers from the bottom of the condensation column or removing high boiler fraction comprising acrylic acid oligomers or a mixture of such bottom liquid comprising acrylic acid oligomers and said high boiler fraction from the condensation column via a sidestream takeoff disposed below the sidestream takeoff for the crude acrylic acid and using it as a quench liquid 1, recirculating the portion of the quench liquid 1 which is not evaporated on cooling the product gas mixture, optionally via the bottom or via the high boiler takeoff of the condensation column or via both and also optionally via a heat exchanger, discharging a portion of the quench liquid 1 from a circuit of the quench liquid 1 as a bleed stream and feeding it to a dissociation vessel and dissociating therein the acrylic acid oligomers contained in the bleed stream of the quench liquid 1 at elevated temperature to acrylic acid, and recycling dissociation gases comprising acrylic acid and escaping from the liquid phase in gaseous form into said circuit of the quench liquid 1 or into the condensation column or into both said circuit of the quench liquid 1 and into the condensation column, either in gaseous, condensed or partially condensed form, which comprises subjecting the dissociation gases to a countercurrent rectification before they are recycled.

2. The process as claimed in claim 1, wherein the C3 precursor is propylene, or acrolein, or a mixture of propylene and acrolein.

3. The process as claimed in claim 1 or 2, wherein the countercurrent rectification of the dissociation gases is carried out in a rectification column which contains exclusively dual-flow trays as separating internals.

4. The process as claimed in claim 1, wherein the acrylic acid oligomers present in the bleed stream of the quench liquid 1 are dissociated without the addition of a dissociation catalyst.

5. The process as claimed in claim 1, wherein the dissociation vessel used is a forced circulation-decompression evaporator.

6. The process as claimed in claim 1, wherein the dissociation of the acrylic acid oligomers contained in the bleed stream of the quench liquid 1 is carried out at a working pressure of from 1 to 2 bar.

7. The process as claimed in claim 1, wherein the bleed stream of the quench liquid 1 is not conducted immediately into the dissociation vessel, but rather conducted into the dissociation vessel via the rectification column attached thereto.

8. The process as claimed in claim 1, wherein the countercurrent rectification of the dissociation gases is effected in a rectification column which is flowed through by an oxygen-containing gas.

9. The process as claimed in claim 1, wherein the dissociation vessel and the rectification column in which the countercurrent rectification of the dissociation gases is effected are flowed through by an oxygen-containing gas.

10. The process as claimed in claim 8 or 9, wherein the oxygen-containing gas is cycle gas.

11. The process as claimed in claim 1, wherein the reflux liquid for the countercurrent rectification of the dissociation gases is generated by direct cooling of the dissociation gases.

12. The process as claimed in claim 1, wherein, for the purposes of polymerization inhibition of the countercurrent rectification of the dissociation gases, quench liquid 1 comprising polymerization inhibitor is added to the reflux liquid.

13. The process as claimed in claim 12, wherein the polymerization inhibitor used is para-methoxyphenol, or phenothiazine, or a mixture of para-methoxyphenol and phenothiazine.

14. The process as claimed in claim 1, wherein the dissociation gases, after their countercurrent rectification, are recycled into the bottom space of the condensation column in gaseous form.

15. The process as claimed in claim 1, wherein the condensation column is one whose separating internals, from bottom to top, are initially dual-flow trays followed by hydraulically sealed crossflow trays.

16. The process as claimed in claim 1, wherein the product gas mixture which may possibly comprise portions of evaporated quench liquid 1 is recirculated into the bottom space of the condensation column and the portion of the quench liquid 1 which does not evaporate when cooling the product gas mixture is recirculated via the bottom of the condensation column.

17. The process as claimed in claim 1, wherein the crude acrylic acid removed from the condensation column via the sidestream takeoff is further purified crystallatively and of the resulting mother liquor is recycled into the condensation column.

18. The process as claimed in claim 17, wherein the crystallization is a suspension crystallization.

19. The process as claimed in claim 18, wherein suspension crystals are removed from the mother liquor in a washing column.

20. A process for preparing polyacrylates comprising polymerizing the suspension crystals of claim 19.

* * * * *